US005773689A

United States Patent [19]
Thompson et al.

[11] Patent Number: 5,773,689
[45] Date of Patent: Jun. 30, 1998

[54] METHOD OF INCREASING EXPRESSION OF FOREIGN GENES IN PLANT CELLS

[75] Inventors: William F. Thompson; Steven L. Spiker; George C. Allen, all of Raleigh; Gerald E. Hall, Jr., Garner; Lisa C. Childs, Raleigh, all of N.C.

[73] Assignee: North Carolina State University, Raleigh, N.C.

[21] Appl. No.: 424,229

[22] Filed: Apr. 19, 1995

Related U.S. Application Data

[63] Continuation of Ser. No. 956,420, Oct. 5, 1992, abandoned.

[51] Int. Cl.[6] ............................. C12N 5/00; C12N 15/00; A01H 1/04
[52] U.S. Cl. .................. 800/205; 435/172.3; 435/320.1; 435/419; 536/24.1; 935/6; 935/22; 935/35; 935/67
[58] Field of Search ........................ 800/205; 435/172.3, 435/240.4, 320.1; 536/24.1, 23.1; 935/3, 65, 67

[56] References Cited

U.S. PATENT DOCUMENTS

| | | | |
|---|---|---|---|
| 5,122,466 | 6/1992 | Stomp et al. | 435/172.3 |
| 5,187,267 | 2/1993 | Comai et al. | 536/23.1 |
| 5,489,520 | 2/1996 | Adams et al. | 435/172.3 |

FOREIGN PATENT DOCUMENTS

| | | |
|---|---|---|
| WO 91/13993 | 9/1991 | WIPO . |
| WO 92/14822 | 9/1992 | WIPO . |
| WO 93/19190 | 9/1993 | WIPO . |
| WO 94/24293 | 10/1994 | WIPO . |

OTHER PUBLICATIONS

P. Meyer, et al., *A Genomic DNA Segment From Petunia Hybrida Leads to Increased Transformation Frequencies and Simple Integration Patterns; Proc. Natl. Acad. Sci.,* vol. 85, pp. 8568–8572, Nov., 1988.

M. Bustos, et al., *Positive and Negative Cis–acting DNA Domains Are Required for Spatial and Temporal Regulation of Gene Expression By A Seed Storage Protein Promoter; The EMBO Journal,* vol. 10, pp. 1469–1479, 1991.

L. Hoffman, et al., *Synthesis and Protein Body Deposition of Maize 15–kd Zein in Transgenic Tobacco Seeds; The EMBO Journal,* vol. 6, pp. 3213–3221, 1987.

L.C. Childs, et al., *Plant Nuclear Scaffold Attachment Regions Functional Analysis Using Transgenes; Molecular Biology of the Cell,* (Suppl.), 1992, 134A Sep., 1992.

G. Hall, Jr., et al., *Nuclear Scaffolds and Scaffold–Attachment Regions in Higher Plants; Proc. Natl. Acad. Sci.,* vol. 88, pp. 9320–9234, Oct. 1991.

C. Sengupta–Gopalan, *Developmentally Regulated Expression of the Bean β–Phaseolin Gene; Proc. Natl. Acad. Sci.,* vol. 82, pp. 3320–3324, May, 1985.

M.E. Eva Ludérus, et al., *Cell* 70, 949–959 (1992).

Peter Breyne et al., *The Plant Cell* 4, 463–471 (1992).

The International Society for Plant Molecular Biology, Abstracts 270, 271, & 407 (1991).

Gerald Hall, Jr., et al., *Proc. Natl. Acad. Sci.* 88, 9320–9324 (1991).

BB Amati et al (1988) *Cell* 54: 967–978.

IK Vasil (1990) *Bio/technology* 8:296–300.

L Mlynárová et al (1994) *Plant Cell* 6:417–426.

GC Allen et al (1993) *Plant Cell* 5:603–613.

JD Watson et al (1987) *Molecular Biology of the Gene* p. 313.

*Primary Examiner*—Bruce R. Campell
*Attorney, Agent, or Firm*—Meyers Bigel Sibley & Sajovec, P.A.

[57] ABSTRACT

Disclosed is a method of making recombinant plant cells having reduced variability of expression and increased levels of expression of foreign genes therein. The method comprises (a) providing a plant cell capable of regeneration; (b) transforming the plant cell with a DNA construct comprising an expression cassette, which construct comprises, in the 5' to 3' direction, a transcription initiation region, a structural gene positioned downstream from the transcription initiation region and operatively associated therewith, and a scaffold attachment region positioned either 5' to the transcription initiation region or 3' to the structural gene, the expression cassette subject to the proviso that T-DNA borders are excluded therefrom. DNA constructs and vectors employed in carrying out the foregoing method are also disclosed, along with plant cells and plants produced thereby.

33 Claims, 1 Drawing Sheet

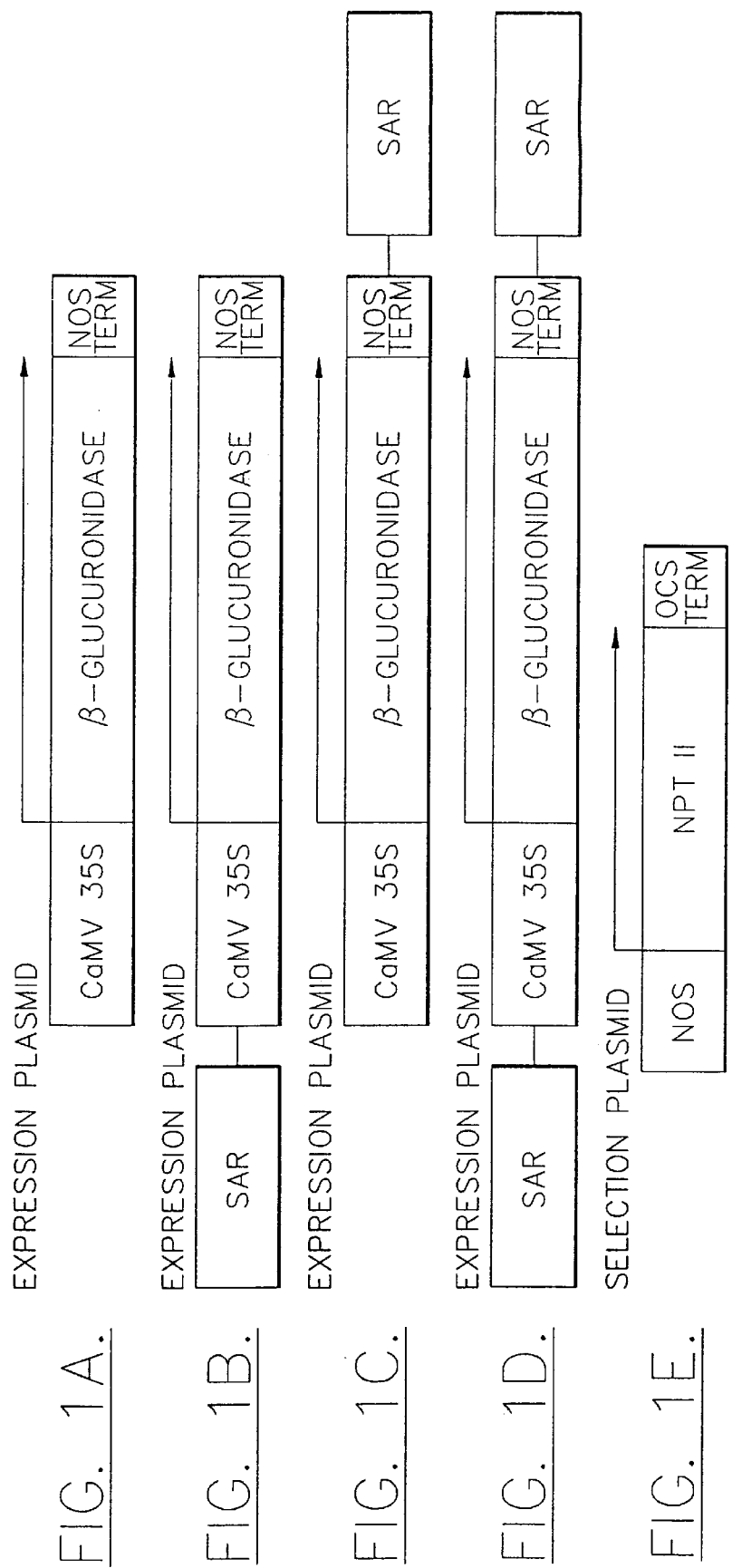

METHOD OF INCREASING EXPRESSION OF FOREIGN GENES IN PLANT CELLS

This is a continuation of application Ser. No. 07/956,420 filed on Oct. 5, 1992 abandoned.

FIELD OF THE INVENTION

The present invention relates to methods for reducing the variability of expression of foreign genes in plant cells, along with DNA constructs for carrying out such methods and the plant cells and plants so produced.

BACKGROUND OF THE INVENTION

Agricultural biotechnology, and particularly plant biotechnology, has become recognized as one of the principal areas for the application of biotechnology techniques. Systems exist for transforming plant cells and regenerating complete plants from the transformed cells; structural gene and gene regulatory regions continue to be identified; and the need for plants with genetically engineered traits such as insect resistance and drought resistance remains strong.

A problem with the expression of foreign genes in plants is the clonal variation in the expression of the same gene in independent transformants: a problem referred to as "position effect" variation. No completely satisfactory method of obviating this problem has yet been developed, and there is accordingly a continued need for solutions to this problem.

SUMMARY OF THE INVENTION

In view of the foregoing, a first aspect of the present invention is a method of making recombinant plant cells having reduced variability of expression and increased levels of expression of foreign genes therein. The method comprises (a) providing a plant cell capable of regeneration; (b) transforming the plant cell with a DNA construct comprising an expression cassette, which construct comprises, in the 5' to 3' direction, a transcription initiation region, a structural gene positioned downstream from the transcription initiation region and operatively associated therewith, and a scaffold attachment region positioned either 5' to the transcription initiation region or 3' to the structural gene, the expression cassette subject to the proviso that T-DNA borders are excluded therefrom. Preferably the transforming step is carried out by bombarding the plant cell with microparticles carrying the expression cassette. The transforming step is preferably followed by regenerating shoots, roots, or both shoots and roots (i.e., an intact plant) from the transformed cells. Preferably the DNA construct comprises, in the 5' to 3' direction, a first scaffold attachment region, a transcription initiation region, a structural gene positioned downstream from the transcription initiation region and operatively associated therewith, a termination region, and a second scaffold attachment region.

A second aspect of the present invention is a DNA construct comprising an expression cassette, which construct comprises, in the 5' to 3' direction, a transcription initiation region, a structural gene positioned downstream from the transcription initiation region and operatively associated therewith, and a scaffold attachment region positioned either 5' to the transcription initiation region or 3' to the structural gene, the expression cassette subject to the proviso that T-DNA borders are excluded therefrom.

A third aspect of the present invention is a DNA construct as given above carried by a plant transformation vector.

A fourth aspect of the present invention is a plant cell containing a DNA construct as given above.

A fifth aspect of the present invention is a recombinant plant comprising transformed plant cells, the transformed plant cells containing a heterologous DNA construct comprising an expression cassette, which construct comprises, in the 5' to 3' direction, a transcription initiation region, a structural gene positioned downstream from the transcription initiation region and operatively associated therewith, and a scaffold attachment region positioned either 5' to the transcription initiation region or 3' to the structural gene, the expression cassette subject to the proviso that T-DNA borders are excluded therefrom.

The foregoing and other objects and aspects of this invention are explained in detail in the specification set forth below.

BRIEF DESCRIPTION OF THE DRAWINGS

FIG. 1A schematically illustrates an expression plasmid containing the cauliflower mosaic virus 35S promoter (CaMV 35S) driving the *Escherichia coli* coding region for β-glucuronidase, with a nopaline synthase gene terminator (NOS TERM).

FIG. 1B schematically illustrates an expression plasmid used to test the effect of a flanking scaffold attachment regions on gene expression. Abbreviations: CaMV35S, cauliflower mosaic virus 35S promoter; β-glucuronidase, coding region of the *Escherichia coli* β-glucuronidase gene; NOS TERM, terminator from the nopaline synthase gene; SAR, scaffold attachment region from the yeast ARS-1 element.

FIG. 1C schematically illustrates an expression plasmid used to test the effect of a flanking scaffold attachment regions on gene expression. Abbreviations are as in FIG. 1B, above.

FIG. 1D schematically illustrates an expression plasmid used to test the effect of a flanking scaffold attachment regions on gene expression. Abbreviations are as in FIG. 1B, above.

FIG. 1E schematically illustrates a selection plasmid consisting of a promoter from the nopaline synthase gene (NOS), a region coding for neomycin phosphotransferase (NPT II), and a terminator from the octapine synthase gene (OCS TERM).

DETAILED DESCRIPTION OF THE INVENTION

The present invention may be carried out in a variety of plants (i.e., vascular plants) and the cells thereof to reduce expression variability therein, including both gymnosperms and angiosperms (i.e., monocots, dicots). Angiosperms are currently preferred.

The term "operatively associated," as used herein, refers to DNA sequences on a single DNA molecule which are associated so that the function of one is affected by the other. Thus, a transcription initiation region is operatively associated with a structural gene when it is capable of affecting the expression of that structural gene (i.e., the structural gene is under the transcriptional control of the transcription initiation region). The transcription initiation region is said to be "upstream" from the structural gene, which is in turn said to be "downstream" from the transcription initiation region.

DNA constructs, or "expression cassettes," of the present invention preferably include, 5' to 3' in the direction of transcription, a first scaffold attachment region, a transcription initiation region, a structural gene operatively associated with the transcription initiation region, a termination sequence including a stop signal for RNA polymerase and a polyadenylation signal for polyadenylation (e.g., the nos terminator), and a second scaffold attachment region. All of these regions should be capable of operating in the cells of the tissue to be transformed. The termination region may be derived from the same gene as the transcriptional initiation or promoter region or may be derived from a different gene.

Scaffold attachment regions (or "SARs"), also called matrix attachment regions (or "MARs"), which are used to carry out the present invention may be of any suitable origin. In general, the SAR of any eukaryotic organism (including plants, animals, and yeast) may be employed, as SARs are highly conserved among the eukaryotes. See, e.g., M. Eva Luderus et al., Cell 70, 949–959 (1992); G. Hall et al., Proc. Natl. Acad. Sci. USA 88, 9320–9324 (1991). For example, animal SARs are shown to be operational in plants in P. Breyne, The Plant Cell 4, 463–471 (1992), and yeast SARs are shown to be operational in plants hereinbelow. Plant SARs may be taken from any suitable plant, including those plants specified above and below; animal SARs may be taken from any suitable animal including mammals (e.g., dog, cat), birds (e.g., chicken, turkey), etc.; and SARs may be taken from other eukaryotes such as fungi (e.g., Saccharomyces cereviceae). Where two scaffold attachment regions are employed, they may be the same or different. The length of the SAR is not critical so long as it retains operability as an SAR, with lengths of from 400 to 1000 base pairs being typical.

The transcription initiation region, which preferably includes the RNA polymerase binding site (promoter), may be native to the host plant to be transformed or may be derived from an alternative sou8rce, where the region is functional in the host. Other sources include the Agrobacterium T-DNA genes, such as the transcriptional initiation regions for the biosynthesis of nopaline, octapine, mannopine, or other opine transcriptional initiation regions, transcriptional initiation regions from plants or woody species other than the host species, transcriptional initiation regions from viruses (including host specific viruses), or partially or wholly synthetic transcription initiation regions. Transcriptional initiation and termination regions are well known. See, e.g., dGreve, J. Mol. Appl. Genet. 1, 499–511 (1983); Salomon et al., EMBO J. 3, 141–146 (1984); Garfinkel et al., Cell 27, 143–153 (1983); and Barker et al., Plant Mol. Biol. 2, 235–350 (1983).

The transcriptional initiation regions may not only include the RNA polymerase binding site, but may also include regions which regulate transcription, where the regulation involves, for example, chemical or physical repression or induction (e.g., regulation based on metabolites or light) or regulation based on cell differentiation, such as associated with leaves, roots, seed, or the like. Thus, the transcriptional initiation region, or the regulatory portion of such region, is obtained from an appropriate gene which is regulated, for example, the 1,5-ribulose biphosphate carboxylase gene, which is light-induced and used for transcriptional initiation, stress-induced genes, heat shock genes which are temperature regulated, wound induced genes, pathogen induced genes, meristem specific genes, genes of viruses specialized to function in plant cells, etc.

Structural genes are those portions of genes which comprise a DNA segment coding for a protein, polypeptide, or portion thereof, possibly including a ribosome binding site and/or a translational start codon, but lacking a transcription initiation region. The term can also refer to copies of a structural gene naturally found within a cell but artificially introduced. The structural gene may encode a protein not normally found in the plant cell in which the gene is introduced or in combination with the transcription initiation region to which it is operationally associated, in which case it is termed a heterologous structural gene. Genes which may be operationally associated with a transcription initiation region of the present invention for expression in a plant species may be derived from a chromosomal gene, cDNA, a synthetic gene, or combinations thereof. Any structural gene may be employed. The structural gene may encode an enzyme to introduce a desired trait into the plant, such as glyphosphate resistance; the structural gene may encode a protein such as a Bacillus thuringiensis protein (or fragment thereof) to impart insect resistance to the plant; the structural gene may encode a plant virus protein or fragment thereof to impart virus resistance to the plant.

The expression cassette may be provided in a DNA construct which also has at least one replication system. For convenience, it is common to have a replication system functional in Escherichia coli, such as ColE1, pSC101, pACYC184, or the like. In this manner, at each stage after each manipulation, the resulting construct may be cloned, sequenced, and the correctness of the manipulation determined. In addition, or in place of the E. coli replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant host. The markers may be protection against a biocide, such as antibiotics, toxins, heavy metals, or the like; provide complementation, by imparting prototrophy to an auxotrophic host: or provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are β-glucuronidase, providing indigo production, luciferase, providing visible light production, NPTII, providing kanamycin resistance or G418 resistance, HPT, providing hygromycin resistance, and the mutated aroA gene, providing glyphosate resistance.

The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature and find particular exemplification in Sambrook et al., Molecular Cloning: A Laboratory Manual, (2d Ed. 1989)(Cold Spring Harbor Laboratory, Cold Spring Harbor, N.Y.).

Vectors which may be used to transform plant tissue with DNA constructs of the present invention are non-Agrobacterium vectors, particularly ballistic vectors, as well as vectors suitable for DNA-mediated transformation.

Microparticles carrying a DNA construct of the present invention, which microparticles are suitable for the ballistic transformation of a plant cell, are also useful for making transformed plants of the present invention. The microparticle is propelled into a plant cell to produce a transformed plant cell, and a plant is regenerated from the transformed plant cell. Any suitable ballistic cell transformation methodology and apparatus can be used in practicing the present invention. Exemplary apparatus and procedures are disclosed in Stomp et al., U.S. Pat. No. 5,122,466; and Sanford and Wolf, U.S. Pat. No. 4,945,050 (the disclosures of all U.S. Patent references cited herein are to be incorporated herein by reference). When using ballistic transformation procedures, the expression cassette may be incorporated into a plasmid capable of replicating in the cell to be transformed. Examples of microparticles suitable for use in such systems include 1 to 5 $\mu$m gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Plants which may be employed in practicing the present invention include (but are not limited to) tobacco (*Nicotiana tabacum*), potato (*Solanum tuberosum*), soybean (*glycine max*), peanuts (*Arachis hypogaea*), cotton (*Gossypium hirsutum*), sweet potato (*Ipomoea batatus*), cassava (*Manihot esculenta*), coffee (*Cofea spp.*), coconut (*Cocos nucifera*), pineapple (*Ananas comosus*), citrus trees (*Citrus spp.*), cocoa (*Theobroma cacao*), tea (*Camellia sinensis*), banana (*Musa spp.*), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), corn (*Zea mays*), wheat, oats, rye, barley, rice, vegetables, ornamentals, and conifers. Vegetables include tomatoes (*Lycopersicon esculentum*), lettuce (e.g., *Lactuea sativa*), green beans (*Phaseolus vulgaris*), lima beans (*Phaseolus limensis*), peas (*Pisum spp.*) and members of the genus Cucumis such as cucumber (*C. sativus*), cantaloupe (*C. cantalupensis*), and musk melon (*C. melo*). Ornamentals include azalea (*Rhododendron spp.*), hydrangea (*Macrophylla hydrangea*), hibiscus (*Hibiscus rosasanensis*), roses (*Rosa spp.*), tulips (*Tulipa spp.*), daffodils (*Narcissus spp.*), petnunias (*Petunia hybrida*), carnation (*dianthus caryophyllus*), poinsettia (*Euphorbia pulcherima*), and chyrsanthemum. Gymnosperms which may be employed to carrying out the present invention include conifers, including pines such as loblolly pine (*Pinus taeda*), slash pine (Pinus elliotii), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The examples which follow are set forth to illustrate the present invention, and are not to be construed as limiting thereof.

EXAMPLE 1

Cell Maintenance for Bombardment

Suspension cultures of Nicotinia Tabacum L, line NT-1, were obtained from G. An, Washington State University. Cells were grown in a medium containing Murashige and Skoog salts (GIBCO Laboratories, Grand Island, N.Y.), 100 mg/liter inositol, 1 mg/liter thiamine HCl, 180 mg/liter $KH_2PO_4$, 30 g/liter sucrose, and 2 mg/liter 2,4-dichlorophenoxyacetic acid. The pH of the medium was adjusted to 5.7 before autoclaving. The cells were subcultured once per week by adding 3 ml of inoculum to 100 ml of fresh medium in 500-ml Erlenmeyer flasks. The flasks were placed on a gyratory shaker at 125 rpm in a growth chamber adjusted to 27° C. and constant light. Four day old cells, in early log phase, were used for bombardment.

Cells were prepared for bombardment by centrifuging 50-ml and resuspending the pellet to a concentration of 1 g/ml which was subsequently diluted to 0.1 g/ml with NT-1 broth. The diluted cells (0.5 ml) were spread as a monolayer onto lens paper on NT-1 agar (2% agar) support in 60×15 mm petri plates. These were kept at room temperature for three hours prior to bombardment.

EXAMPLE 2

Plasmid DNA and Microprojectile Coating

The $\beta$-glucuronidase (GUS) gene was used to measure expression and the neomycin phosphate transferase gene (nptII) was used for selection for stable transformation. The plasmids used in these transformation experiments are summarized in Table 1 below. All plasmids were amplified in *Escherichia coli* strain DH5 alpha and were isolated by the Qiagen plasmid MAXIPREP™ kit. For each of the co-transformation plasmid mixtures, the molar ratio of GUS gene to nptII gene was 4:1. The DNA mixtures were associated with 1.0 um gold microprojectiles using $CaCl_2$/spermidine precipitation.

TABLE 1

PLASMID SUMMARY

| PLASMID | DESCRIPTION |
|---|---|
| pGA-1 | The EcoR1 fragment containing the TRP/ARS-1 Scaffold Attachment Region of yRP7 (B. Amati and S. Gasser, Cell 54: 967–978 (1988)) was cloned into the unique EcoR1 site in the pJKK mf(1)(J. Kirshman and J. Cramer, Gene 68: 163–165 (1988)) vector polylinker. |
| pGCA-3 | The HindIII fragment of pGA-1 containing the ARS-1 cloned into the unique HindIII site in the Bluescribe pBSM13(-) vector purchased from Stratagene. |
| pGCA8 | Identical to pGCA3 except the EcoR1 sites have been destroyed with Mung Bean nuclease and religated. |
| pGCA6 | EcoR1 fragment of WPF144 (from W. Fitzmaurice) containing the CaMV 35S promoter driving the dihydrofolate reductase (dhfr) gene with a nos terminator cloned into the unique EcoR1 site of pBI221. |
| pGCA12 | Pst1/Kpn1 fragment of pGCA6 containing the CaMV 35S promoter driving the GUS gene with a nopaline synthase terminator and CaMV35S promotor driving the dhfr gene with a nos terminator cloned into the Pst1/Kpn1 site of the Bluescript II KS vector polylinker. Bluscript II was purchased from Stratagene. The BSSH2 site in the nos terminator of the GUS gene also has been destroyed with Mung Bean nuclease. |
| pGCA776 | XbaI fragment of pGCA8 containing ARS-1 was cloned into the unique Spe site of pGCA12. This resulted in ARS-1 in a correct orientation at the 5' end of the fragment containing the CaMV35S promoter driving the GUS gene with a nos terminator and CaMV35S promoter driving the dhfr gene with a nos terminator. |
| pGCA887 | HindIII/Sal 1 fragment of pGCA8 containing the ARS-1 cloned into the Hind III/Sal 1 site in the polylinker of the Bluescript pBC KS(+) vector purchased from Stratagene. The resulting plasmid has unique multiple cloning restriction sites flanking the ARS-1. |
| pBI221 | The Hind III/EcoR1 fragment from pBII21 (R. Jefferson et al., EMBO J. 6: 3901–3907 (1987)) containing the CaMV35S promoter driving the GUS gene with a nos terminator was cloned into pUC19. This vector was purchased from Clontech. This expression plasmid is schematically illustrated in FIG. 1A. |
| pGCA905 | Not I/EcoR1 fragment of pGCA776 containing the CaMV35S promoter driving the GUS gene with a nos terminator and CaMV35S promoter driving the dhfr gene with a nos terminator cloned into the NOT I/EcoR1 site in the pBC KS(+) vector purchased from Stratagene. The resulting plasmid has ARS-1 in correct orientation 5' of the GUS reporter gene. This expression plasmid was is schematically illustrated in FIG. 1B. |
| pGCA1055 | EcoR1/SacII fragment of pGCA12 containing the CaMV35S promoter driving the GUS gene with a nos terminator cloned into the uniqu EcoR1/SacII of PGCA887. The resulting plasmid has ARS-1 in correct orientation 3' of the GUS reporter gene. This expression plasmid is schematically illustrated in FIG. 1C. |
| pGCA984 | EcoR1/SacII fragment of pGCA776 containing the ARS-1 5' of the CaMV35S promoter driving the GUS gene with a nos terminator cloned into the unique EcoR1/SacII site of pGCA887. The resulting plasmid has ARS-1 in correct orientation flanking the GUS reporter gene. This expression plasmid is schematically illustrated in FIG. 1D. |
| pUCNK1 | This plasmid (L. Herrera-Estrella et al., in Plant Molecular Biology Manual B1: 1–22 (S. Gelvin and R. Schilperoot, Eds. 1988)) contains a nopaline synthase promoter (nos) driving neomycin phosphotransferase (nptII) with an octapine synthase terminator. Expression of this plasmid confers kanamycin resistance in plant cells. This selection plasmid is schematically illustrated in FIG. 1E. |

EXAMPLE 3

Particle Accelerator

A DuPont PDS-1000 biolistic device was used in all microprojectile bombardments as described by the manufacturer. Briefly, the target cells were placed below the microprojectiles and the chamber was evacuated. The high pressure chamber was pressurized to 1500 psi with helium gas which ruptures a disk. The resulting shock wave forces a Kapton disk coated with the microprojectiles onto a steel screen. The gold microprojectiles previously coated with DNA as described in Example 2 above continue onward to penetrate the NT-1 cells.

EXAMPLE 4

Recovery and Histochemical Screening of Stable Transformants

After bombardment, the petri plates were sealed with parafilm and incubated for 24 hours at 27° Centigrade under constant light. The lens paper was then carefully removed and transferred to fresh NT-1 agar plates containing 300 μg per ml kanamycin. Kanamycin resistant microcalli began to appear in approximately 3 weeks. The isolated microcalli were then transferred to fresh NT-1 agar containing 300 μg per ml kanamycin. Pieces of the microcalli were removed and placed into sterile microfuge tubes. The microcalli were then histochemically screened by adding 200 μL of 5-bromo-3-chloro-3-indolyl-β-D-glucuronic acid (X-gluc) and incubated for 24 hours at 37° Centigrade. Results (data not shown) indicated that the double SAR construct illustrated in FIG. 1D gives higher levels of gene expression when compared to the other constructs and increases the percentage or fraction of transformants with detectable expression of the GUS reporter gene. Both single SAR constructs (FIG. 1B; FIG. 1C) produced intermediate GUS expression levels, whereas when no SAR was present expression levels were extremely low.

The foregoing examples are illustrative of the present invention, and are not to be construed as limiting thereof. The invention is described by the following claims, with equivalents of the claims to be included therein.

That which is claimed is:

1. A method of making recombinant plant cells having increased expression of foreign genes therein, said method comprising:

providing a plant cell capable of regeneration;

transforming said plant cell with a DNA construct comprising, in the 5' to 3' direction, a transcription initiation region functional in plant cells, a structural gene positioned downstream from said transcription initiation region and operatively associated therewith, and a scaffold attachment region positioned either 5' to said transcription initiation region or 3' to said structural gene, said DNA construct subject to the proviso that T-DNA borders ate excluded therefrom;

wherein expression of the structural gene is increased compared to that which would occur in the absence of said scaffold attachment regions.

2. A method according to claim 1, which construct comprises, in the 5' to 3' direction, a first scaffold attachment region, a transcription initiation region functional in plant cells, a structural gene positioned downstream from said transcription initiation region and operatively associated therewith, and a second scaffold attachment region.

3. A method according to claim 1, wherein said transforming step is carried out by bombarding said plant cell with microparticles carrying said expression cassette.

4. A method according to claim 1, wherein said plant cell resides in a plant tissue capable of regeneration.

5. A method according to claim 1, further comprising the step of regenerating shoots from said transformed plant cells.

6. A method according to claim 1, further comprising the step of regenerating roots from said transformed plant cells.

7. A method according to claim 1, further comprising the step of regenerating a plant from said transformed plant cells.

8. A method according to claim 1, wherein said plant cells are monocot cells.

9. A method according to claim 1, wherein said plant cells are dicot cells.

10. A method according to claim 1, wherein said plant cells are gymnosperm plant cells.

11. A method according to claim 1, wherein said first and second scaffold attachment regions are yeast scaffold attachment regions.

12. A method according to claim 1, wherein said first and second scaffold attachment regions are plant scaffold attachment regions.

13. A DNA construct comprising, in the 5' to 3' direction, a transcription initiation region functional in plant cells, a structural gene positioned downstream from said transcription initiation region and operatively associated therewith, and a scaffold attachment region positioned either 5' to said transcription initiation region or 3' to said structural gene;
which DNA construct is carried by a plant transformation vector subject to the proviso that said plant transformation vector is not *Agrobacterium tumefaciens*.

14. A DNA construct according to claim 13, which construct comprises, in the 5' to 3' direction, a first scaffold attachment region, a transcription initiation region functional in plant cells, a structural gene positioned downstream from said transcription initiation region and operatively associated therewith, and a second scaffold attachment region.

15. A DNA construct according to claim 14, wherein said first and second scaffold attachment regions are yeast scaffold attachment regions.

16. A DNA construct according to claim 14, wherein said first and second scaffold attachment regions are plant scaffold attachment regions.

17. A recombinant plant comprising transformed plant cells, said transformed plant cells containing a heterologous DNA construct comprising, in the 5' to 3' direction, a transcription initiation region functional in plant cells, a structural gene positioned downstream from said transcription initiation region and operatively associated therewith, and a scaffold attachment region positioned either 5' to said transcription initiation region or 3' to said structural gene, said DNA construct subject to the proviso that T-DNA borders are excluded therefrom.

18. A recombinant plant according to claim 17, which construct comprises, in the 5' to 3' direction, a first scaffold attachment region, a transcription initiation region functional in plant cells, a structural gene positioned downstream from said transcription initiation region and operatively associated therewith, and a second scaffold attachment region.

19. A recombinant plant according to claim 18, wherein said first and second scaffold attachment regions are yeast scaffold attachment regions.

20. A recombinant plant according to claim 18, wherein said first and second scaffold attachment regions are plant scaffold attachment regions.

21. A recombinant plant according to claim 18, further comprising a termination sequence positioned downstream from said structural gene and operatively associated therewith, said termination sequence positioned 5' to said second scaffold attachment region.

22. A recombinant plant according to claim 17, which plant is a monocot.

23. A recombinant plant according to claim 17, which plant is a dicot.

24. A recombinant plant according to claim 17, which plant is a dicot selected from the group consisting of tobacco, potato, soybean, peanuts, cotton, and vegetable crops.

25. A recombinant plant according to claim 17, which plant is a gymnosperm.

26. A plant cell containing a DNA construct, said DNA construct comprising, in the 3' direction, a transcription initiation region functional in plant cells, a structural gene positioned downstream from said transcription initiation region and operatively associated therewith, and a scaffold attachment region positioned either 5' to said transcription initiation region or 3' to said structural gene, said DNA construct subject to the proviso that T-DNA borders are excluded therefrom.

27. A plant cell according to claim 26, which plant cell is a dicotyledonous plant cell.

28. A plant cell according to claim 26, which plant cell is a monocotyledonous plant cell.

29. A plant cell according to claim 26, which plant cell is a gymnosperm plant cell.

30. A method of making recombinant tobacco plant cells having increased expression of foreign genes therein, said method comprising:
providing a tobacco plant cell capable of regeneration;
transforming said tobacco plant cell with a DNA construct comprising, in the 5' to 3' direction, a transcription initiation region functional in plant cells, a structural gene positioned downstream from said transcription initiation region and operatively associated therewith, and a yeast scaffold attachment region positioned either 5' to said transcription initiation region or 3' to said structural gene, said DNA construct subject to the proviso that T-DNA borders are excluded therefrom;
wherein expression of the structural gene is increased compared to that which would occur in the absence of said scaffold attachment regions.

31. A DNA construct comprising, in the 5' to 3' direction, a transcription initiation region functional in plant cells, a structural gene positioned downstream from said transcription initiation region and operatively associated therewith, and a yeast scaffold attachment region positioned either 5' to said transcription initiation region or 3 ' to said structural gene;
which DNA construct is carried by a plant transformation vector, subject to the proviso that said plant transformation vector is not *Agrobacterium tumefaciens*.

32. A recombinant tobacco plant comprising transformed tobacco plant cells, said transformed tobacco plant cells containing a heterologous DNA construct comprising, in the 5' to 3' direction, a transcription initiation region functional in plant cells, a structural gene positioned downstream from said transcription initiation region and operatively associated therewith, and a yeast scaffold attachment region positioned either 5' to said transcription initiation region or 3' to said structural gene, said DNA construct subject to the proviso that T-DNA borders are excluded therefrom.

33. A tobacco plant cell culture comprising cells containing a DNA construct, said DNA construct comprising, in the 5' to 3' direction, a transcription initiation region functional in plant cells, a structural gene positioned downstream from said transcription initiation region and operatively associated therewith, and a yeast ARS-1 scaffold attachment region positioned either 5' to said transcription initiation region or 3' to said structural gene, said DNA construct subject to the proviso that T-DNA borders are excluded therefrom.

* * * * *

UNITED STATES PATENT AND TRADEMARK OFFICE
CERTIFICATE OF CORRECTION

PATENT NO.  : 5,773,689
DATED       : Jun. 30, 1998
INVENTOR(S) : William F. Thompson, et al It is certified that error appears in the above-identified patent and that said Letters Patent is hereby corrected as shown below:

In claims 1, at column 8, line 55, replace "ate" with --are.

Col. 10, lines 15-16, replace "said DNA construct comprising, in the 3' direction,' with --said DNA construct comprising, in the 5' to 3' direction--.

Signed and Sealed this

First Day of December, 1998

BRUCE LEHMAN

Attest:

Attesting Officer

Commissioner of Patents and Trademarks